United States Patent [19]

Barcelona et al.

[11] Patent Number: 4,803,869
[45] Date of Patent: Feb. 14, 1989

[54] FLOW-THROUGH ANALYTICAL MEASUREMENT APPARATUS AND METHOD

[75] Inventors: Michael J. Barcelona, Urbana; Edward E. Garske, Mundelein; Michael R. Schock, Champaign, all of Ill.

[73] Assignee: Board of Trustees, University of Illinois, Urbana, Ill.

[21] Appl. No.: 53,302

[22] Filed: May 22, 1987

[51] Int. Cl.⁴ .......................................... G01N 33/18
[52] U.S. Cl. .................................... 73/53; 73/61.1 R
[58] Field of Search .............................. 73/53, 61.1 R

[56] References Cited

U.S. PATENT DOCUMENTS

| | | | |
|---|---|---|---|
| 2,966,055 | 12/1960 | Tracht et al. | 73/53 X |
| 2,976,728 | 3/1961 | Brogan et al. | 73/61.1 R X |
| 3,214,964 | 11/1965 | Davis | 73/53 |
| 3,250,118 | 5/1966 | Johnson, Jr. | 73/53 |
| 3,512,398 | 5/1970 | Hrdina | 73/61.1 R |

FOREIGN PATENT DOCUMENTS 1117213 6/1968 United Kingdom ................... 73/53

Primary Examiner—John Chapman
Assistant Examiner—Joseph W. Roskos
Attorney, Agent, or Firm—Philip Hill

[57] ABSTRACT

An improved portable apparatus is provided for the flow-through measurement of analytical parameters of liquids, particularly ground water. A concave end design, employing transparent materials, together with selected transparent pipe sections, affords an adjustable cell volume to minimize turbulence at the point of analysis, while also monitoring electrode fouling.

25 Claims, 3 Drawing Sheets

FLOW-THROUGH ANALYTICAL MEASUREMENT APPARATUS AND METHOD

BACKGROUND OF THE INVENTION

Analysis of natural liquids at some distance from their natural situs is typically difficult because of changes in the sample environment as it is moved from the situs, questions as to the representative nature of the sample, and possible interactions with sampling and test equipment. Analysis of ground water, whether from aquifers, springs or surface streams, is especially sensitive to sampling and measuring conditions if accurate data are to be obtained.

Monitoring of water supplies is conducted periodically fo reasons of public health and regulatory compliance. Monitoring is likewise conducted in random situations where new wells are brought into service and where underground flows of water and their chemical characteristics are sought to be defined. Proper sampling of ground water seeks a close approximation to conditions where a well is producing water typical of the aquifer formation and not water modified chemically by conditions induced by the well itself. Geothermal liquids present different and complex problems generally due to high pressure, high temperature, and instability. Various techniques for the collection and analysis of ground water samples have been studied and guidelines have been developed by the Water Resources Division of the United States Geological Survey. However, improved sampling and analysis to provide a true picture of ground water supplies remains a matter of concern, particularly in a time when public awareness and concern for the nature and preservation of the environment is highly significant.

Analysis of ground water involves the determination of many parameters, some being very sensitive to analytical conditions. Such sensitive parameters include pH, oxidation-reduction (redox) potential (Eh), specific conductance, dissolved oxygen, temperature, and ferrous iron. Other mineral parameters are less sensitive to handling conditions. Other specialized parameters relate to colloidal and biological characteristics of the in situ ground water.

Despite extensive study given to this problem, there remains a need for methodology providing greater sensitivity and greater assurance of determination under precise conditions in ground water.

SUMMARY OF THE INVENTION

The invention of this disclosure relates to an improved flow-through transparent analytical measurement apparatus, and method for its use, intended for the direct determination of characteristic parameters of liquid samples, such as ground water. The invention further relates to the adaptation of the apparatus for portable field use in a kit form.

It is an object of this invention to provide apparatus for use at a distance from the sampling point with a minimum of alteration of sample characteristics prior to testing.

It is a further object of this invention to provide a cell affording a zone having parabolic or conically shaped end sections for a plurality of interchangeable electrode measurements, thus affording optimized, non-turbulent flow under controlled conditions of temperature and pressure, approaching those of the sampled liquid in its natural state.

A further object of this invention is to provide a non-turbulent zone adjustable in volume as required for the analytical conditions peculiar to any parameter determination.

Other objects will become apparent from the discussion below.

BRIEF DESCRIPTION OF THE DRAWINGS

The following drawings are illustrative, without limitation, of aspects of the invention of this disclosure.

DESCRIPTION OF THE INVENTION

Figure 1:
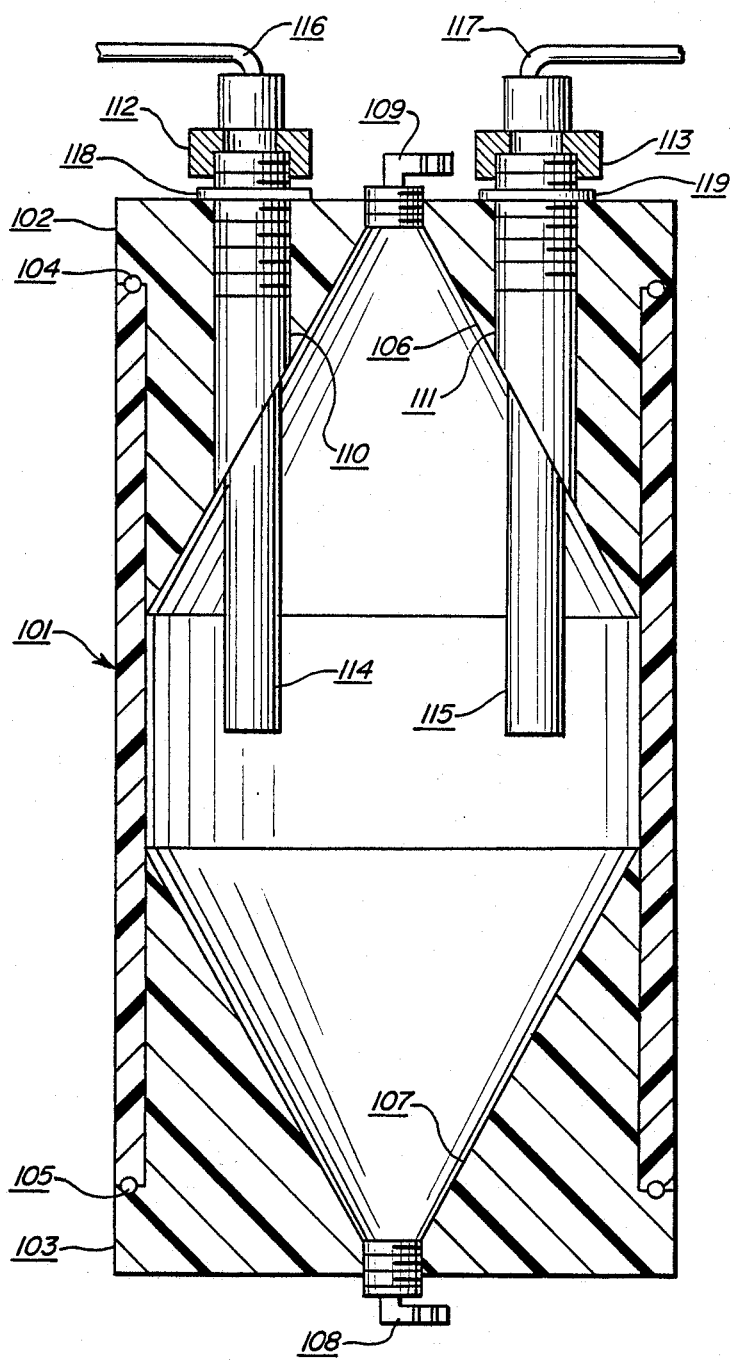
FIG. 1 presents a cross-section view of the measurement apparatus.
Figure 2:
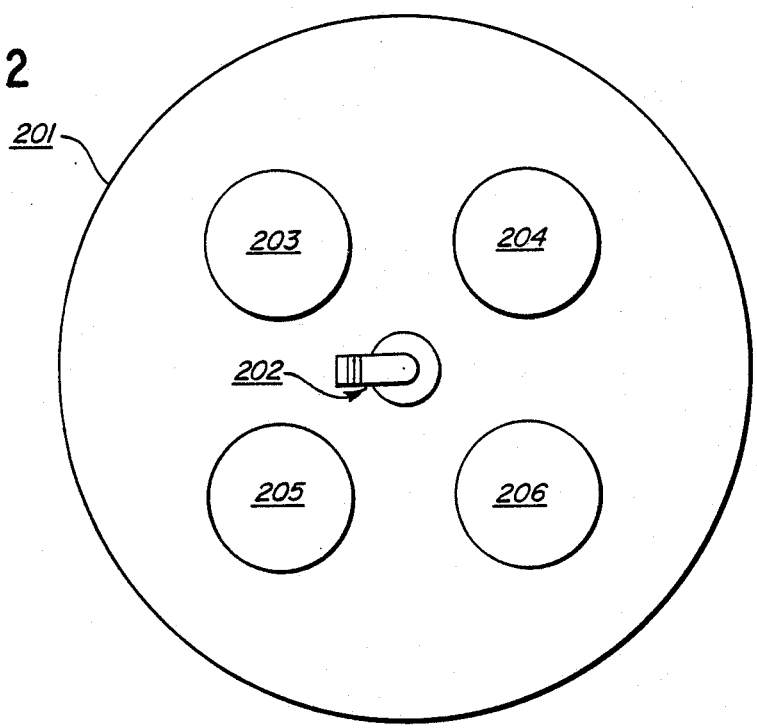
FIG. 2 presents a top view of such measurement apparatus.

The invention of this disclosure relates to improved apparatus for representative measurement of pertinent characteristics of liquids such as ground water and to an improved method for conducting such analytical measurements. Sampling of ground water sources and cells for electrochemical measurement of water parameters both require great care in assuring proper analytical determinations which reflect natural environmental conditions.

Such measurements of solution chemistry parameters are essential to meaningful geochemical and monitoring investigations of ground water systems. This invention provides an improved cell for electrometric measurements in pumped ground water whereby an efficient measure of well purging operations may be achieved. When constant values of selected parameters are achieved, samples may then be taken for subsequent chemical analysis with increased confidence in their representative nature.

In achieving meaningful measurements of ground water parameters, care must be taken to transport the water sample under conditions with the least possible opportunity for significant alteration. Further, the test cell must afford the least possible change from the natural environment of the sample. In the apparatus of this invention, an upright cell is provided to afford an upward flow of water past the selected electrodes or sensors. Upon entry into the cell, the water sample is introduced into a concave zone of rapidly increasing diameter, which may be parabolic, or preferably conical, in nature. The linear velocity of the pumped water sample is markedly decreased so that the water flows upwardly in a substantially quiescent, or non-turbulent, manner. This affords the most representative contact with the respective electrodes or sensors, and thus affords the most typical and reproducible test values.

Upon leaving the upper end of the cell such a concave arrangement again insures the least likelihood of back-mixing and possible fouling of measurements. However, at this point a flat inner end wall may be employed with the upper cylindrical block. This is possible, even though some back-mixing may occur, because the linear velocity of the water sample will be low enough for such mixing to be kept at a distance from the electrode, or sensor, area and thus have no effect upon the analytical measurements.

The apparatus of this invention is designed to afford four or more electrode sensors in a cell fashioned to avoid the problems inherent in existing cells used for such purposes, such as, for example, streaming potential interference, gas bubble accumulation, and poor electrode response. The novel cell is rugged, portable, water-tight in transit, and battery-operated. It has been found to function satisfactorily even in cold weather.

The flow cell of this invention is easily cleaned and maintained for channelling a selected sample flow vertically past electrode sensors for a variety of chemical parameter determinations. These parameters include pH, redox potential (Eh), dissolved oxygen, ammonia, sulfide ion, and conductivity, among others. The novel cell structure is made of transparent material for ready detection of fouling or gas accumulation which will alter the electrometric signals and provide false readings. Gas or foreign matter can be removed easily by a rapid dismantling, cleaning, and reassembly operation. Electrode and other sensor malfunctions can readily be noted by calibration procedures and, where necessary, electrodes may be replaced quickly with no need to cease or reduce the flow of the pumped sample. Conventional electrodes and sensors are used so that special connections are not required. The volume of the cell can be readily adjusted.

A representative example of the cell design of this invention is presented in the cross-sectional representation of FIG. 1. A transparent, hollow, cylindrical pipe section 101 is fitted at each end with solid transparent blocks 102 and 103, machined to afford a snug fit along most of their walls with the interior surface of the pipe section. The outer end wall of each block extends outwardly to provide a diameter corresponding approximately to the outside diameter of the pipe section, with each piece being adapted to receive O-rings 104 and 105 for effecting a liquid-tight seal. The two transparent blocks are machined to convert the respective interior walls (whose diameters are selected to provide the snug fit with the inside diameter of the pipe section) to concave conical interior walls 106 and 107. Each transparent block is also machined to provide a centrally positioned threaded opening for receiving conventionally threaded lines, for example, threaded entry line 108 and threaded exit line 109. Solid, transparent block 102 is further machined to provide a plurality of circular threaded glands 110 and 111, adapted to receive conventional electrode assemblies 112 and 113. The electrode assemblies are fitted, respectively, with sensors 114 and 115, meter connectors 116 and 117 extending to meter means (not shown), and seals 118 and 119.

A top view of the measurement apparatus cell includes such a flat outer end wall 201, the placement of the central threaded opening with exit line 202 in place, and the respective placements of threaded glands 203, 204, 205, and 206.

The cell design of this invention readily permits operation under the entire range of flow velocities and pressures typically encountered in the field. The cell is intended for use with flow velocities up to about 1 liter/minute and excess flowage may be diverted without effect on the accuracy of measurements. Back pressures up to several atmospheres may be employed to prevent degassing and resultant changes in pH or mineral precipitation.

The transparent, hollow pipe section and the cylindrical blocks may be fashioned from any suitable transparent material but, in practice, preferred materials are chemically inert plastics, and a particularly preferred material is polymethyl methacrylate (PMMA). In practice, PMMA pipe having a 5-inch O.D. is generally employed. A preferred length is about 10 inches, although the length may generally vary from about 1.5 to about 5 times the interal diameter of the pipe section.

The transparent, cylindrical block, is typically selected to extend about 3 inches into the interior of the pipe section, with an overall length of about 4 inches, although the overall length may generally vary from about 0.5 to about 1.0 time the internal diameter of the pipe section.

The central portion of the length of the pipe section, which defines the volume which receives the sensor sections of the electrodes, is taken as that portion of the pipe length not fitted with either of the solid blocks and should have a length of at least about 2 inches and may be selected to vary greater than that as desired to provide a non-turbulent vertical liquid flow.

Use of a clear, transparent construction for the measurement cell structure permits convenient monitoring of the sensor surfaces for coating with colloidal material or mineral precipitates. The concave shape of the ends of the cell, which may be parabolic, or preferably conical, coupled with the vertically-directed flow serves to minimize the trapping of air bubbles that is so common in conventional cylindrical or rectangular in-line cell designs. The clear view of the electrodes permits the detection of bubbles that adhere to electrode surfaces. Such bubbles can often be removed by gentle tapping of the electrodes. In any event, bubble removal is essential if one is to obtain accurate readings. The size and shape of the cell reduces the linear rate of flow past the pH electrode and thus eliminates the "streaming potential", a potential difference generated by movement of water containing ionic solutes through small lines anf flow chambers and leading to erroneous pH readings.

A preferred volume for the cell is about 500 ml. While smaller volumes may conserve sample water, care must be taken not to decrease cell size to the point where a streaming potential is induced by an increase in flow rate past the electrode.

Figure 3:
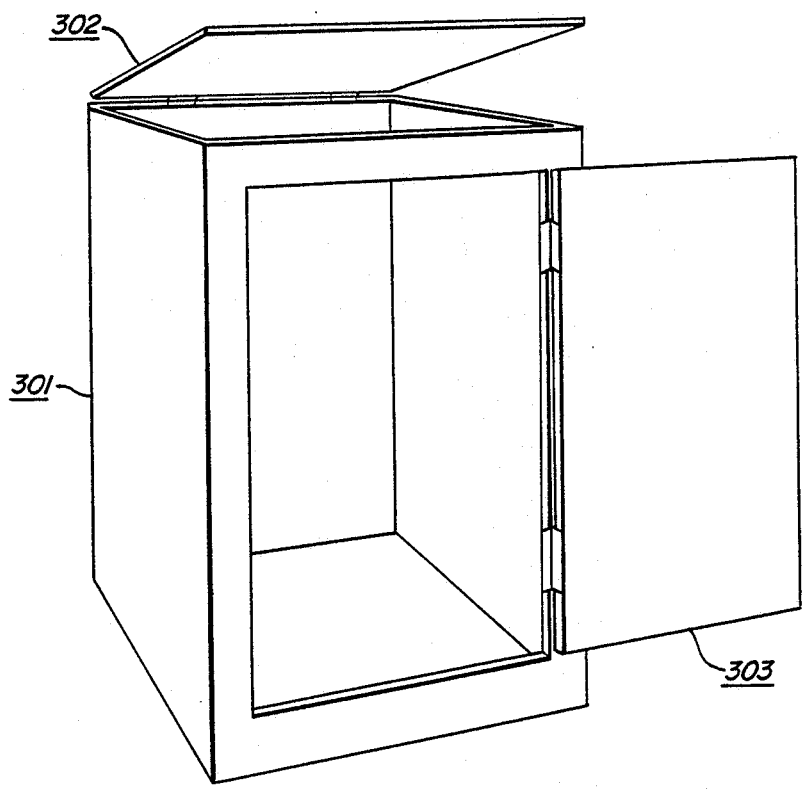
FIG. 3 presents a perspective view of the front of a portable housing for an analysis kit.

When the cell of this invention is used in the field it may be afforded as part of a kit, employing as a first component the protective assembly shown in FIG. 3. Portable box 301 is fitted with a hinged top section 302 and a transparent plastic door 303 that opens for easy access. The cell assembly can be braced inside the box and connections (not shown) made to a second housing component (not shown) which contains the requisite meters for measurements and battery for power. All sampling lines and housing components can be insulated, as desired, to minimize temperature differentials between aquifer or other aqueous zone and the analytical assembly.

It is not possible to completely avoid intrinsic changes in sample chemistry as the water sample is withdrawn from its natural environment in relatively deep wells. Some degassing, resulting pH change, and solubility changes, usually related to liberation of carbon dioxide and a resultant shift in pH, will occur with a decrease in ambient pressure as samples are pumped to the surface. Accordingly, a preferred use of the cell of this invention will be found with relatively shallow wells, having a depth no greater than about 200 feet, where such pressure effects have been found to be substantially absent.

When operating the cell system of this invention in association with a well, the sampling line extends down to the water reservoir and is connected to a suitable sampling or purging pump, such as a bladder pump, operated with inert gas. Flow rate may be adjusted as desired but preferably should be about 700 ml/min. or less for best results. This rate represents a balance between minimizing streaming potential effects, pressure drop effects, and time of contact with sampling lines. Conductivity measurements are customarily made employing a cell inserted in the sampling line. When electrode readings have stabilized it may generally be assumed that stagnant water from the well has been removed and that the following sample represents formation water.

The following example is illustrative, without limitation, of the flow-through analytical measurement apparatus of this invention.

EXAMPLE I

A flow-through cell, having substantially the configuration shown in FIG. 1, was employed in the analysis of water contained in a shallow aquifer system. The cell system was constructed of a PMMA (Plexiglass ®) pipe section, 5" O.D.×10" length. The solid blocks were of the same material, machined to have a 5" diam. outer wall and a total length of 4", the cap being 1" in length and the remainder being machined to slip snugly into the pipe section. The internal walls of the solid blocks were machined out to provide concave cones. When assembled, a central 2" length of the pipe section was free of any contact with the solid blocks. The internal volume was approximately 500 ml. The cap sections of the two blocks were held against the ends of the pipe section with long bolt assemblies, each closing containing a recessed O-ring for effecting a water-tight seal.

The upper solid block was additionally fitted with standard ½" NPT electrodes, for determination of pH and Eh, and a sensor for temperature.

Water lines, made of Tygon ® tubing, were attached to the entry and exit lines to afford an upward vertical flow of water. All electrodes and sensors were connected to meters contained in a separate metering box. A flow-through conductivity cell was placed in the water sampling line ahead of the cell.

Figure 4:
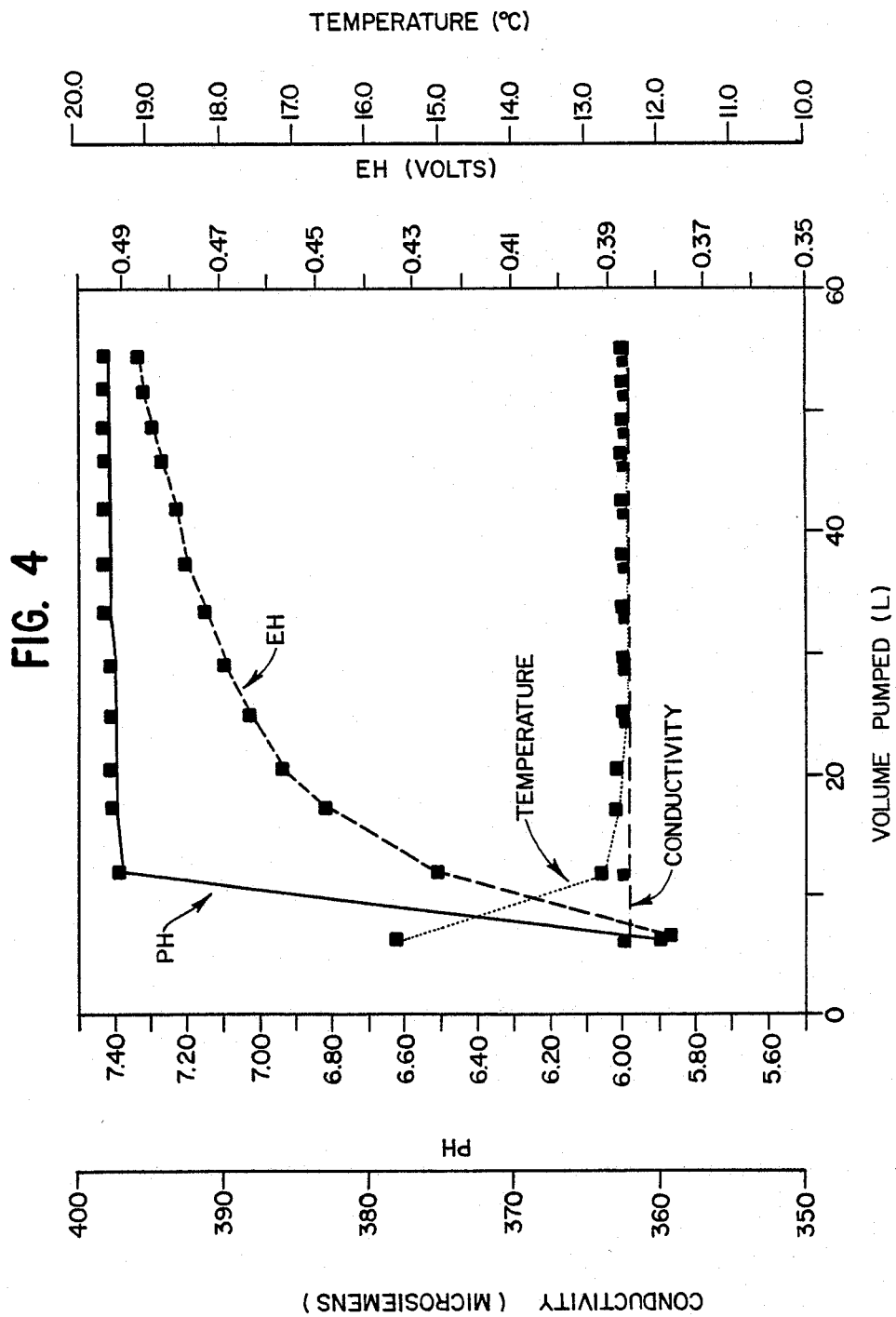
FIG. 4 presents, in graphical form, parameter measurements taken during a typical ground water analysis performed with the apparatus of this invention.

All electrodes were first calibrated against buffer solution, with allowance made for ambient temperature. In the method for use of this apparatus, pumping was begun at a rate of 700 ml/min. and exit volume was measured. After a period of about 10 minutes, measurements were taken at intervals of 5-7 minutes and plotted as shown in FIG. 4. Conductivity quickly reached an equilibrium reading. After pumping only about 10 liters (ca. 14 minutes) both water temperature and pH gave nearly constant readings. On the other hand, the redox potential (Eh) came to equilibrium much more slowly. After passage of some 60 liters of water through the cell system, samples were taken for later analyses for selected minerals.

We claim:

1. Flow-through analytical measurement apparatus, for the analytical determination of characteristic parameters of a liquid sample, comprising:
   (a) a transparent, hollow cylindrical pipe section, to be maintained in a vertical position during analysis, having first and second open ends;
   (b) first and second transparent, solid, cylindrical blocks, each having one flat outer end wall whose diameter substantially corresponds to the outside diameter of the cylindrical pipe section, and one concave interior end wall whose diameter is selected to be snugly received by the respective first or second open ends of the hollow cylinder, thereby defining an enclosed volume described by the inner dimensions of a central portion of the length of the hollow cylindrical pipe section and the concave interior walls of the first and second cylindrical blocks;
      (i) said first cylindrical block having a centrally located threaded opening therethrough, to receive a line for the upwardly flowing entry of the liquid sample;
      (ii) said second cylindrical block having a centrally located threaded opening therethrough, to receive a line to accommodate the exit of the liquid sample; and
      (iii) said second cylindrical block additionally having a plurality of threaded openings extending therethrough and spaced about the centrally located opening, to receive at the flat outer wall of the second cylindrical block a plurality of selected analytical electrodes or sensors;
   (c) sealing means for effecting a liquid-tight seal between the open ends of the hollow cylindrical pipe section and the respective flat outer walls of the cylindrical blocks;
   (d) a plurality of interchangeable threaded electrodes or sensors, sealably fitted to the flat outer wall of the second cylindrical block and extending into a central portion of the enclosed volume; and
   (e) external meter means, attached to said electrodes or sensors for measurement of the characteristic parameters associated therewith.

2. The apparatus of claim 1 wherein the concave interior end walls of the cylindrical blocks are concave conical interior end walls.

3. The apparatus of claim 1 wherein the concave interior end walls of the cylindrical blocks are concave parabolic interior end walls.

4. The apparatus of claim 1 wherein the hollow cylindrical pipe section is constructed of a transparent plastic material.

5. The apparatus of claim 1 wherein the hollow cylindrical pipe section is constructed of polymethyl methacrylate pipe.

6. The apparatus of claim 1 wherein the solid cylindrical blocks are constructed of a transparent plastic material.

7. The apparatus of claim 1 wherein the solid cylindrical blocks are constructed of polymethyl methacrylate.

8. The apparatus of claim 1 wherein the length of the hollow cylindrical pipe section is from about 1.5 to about 5 times the internal diameter of said pipe section.

9. The apparatus of claim 1 wherein the overall length of the solid cylindrical blocks is from about 0.5 to about 1.0 times the internal diameter of said pipe section.

10. The apparatus of claim 1 wherein the length of the pipe section is selected to provide inner dimensions of a central portion of said pipe length sufficient to avoid turbulent liquid flow in the central portion of the enclosed volume defined thereby.

11. The apparatus of claim 1 wherein the liquid sample is ground water and the characteristic parameters are pH, oxidation-reduction potential, conductance, and temperature.

12. The apparatus of claim 11, contained within a portable housing additionally fitted with a sampling line and a pump suited for field measurement of water streams or pools.

13. The apparatus of claim 1 wherein the interior end wall of the second cylindrical block is flat rather than concave.

14. In an improved method for the flow-through analysis of ground water samples, comprising the steps of:
  (1) pumping a stream of ground water from a representative source continuously to an analytical cell, said cell being fitted for the measurement of one or a plurality of selected parameters;
  (2) introducing the ground water stream into a bottom section of the analytical cell, whereby an upward flow is effected;
  (3) continuously measuring one or more selected parameters until constant values of the measured, selected parameters are achieved;
  (4) effecting measurement of all of the selected parameters; and
  (5) discharging the analyzed ground water stream from a top section of the analytical cell; the improvement wherein such measurements are achieved under conditions selected to substantially maintain the natural characteristics of the water sample by use of a selected analytical cell, said cell comprising:
  (a) a transparent, hollow cylindrical pipe section, to be maintained in a vertical position during analysis, having first and second open ends;
  (b) first and second transparent, solid, cylindrical blocks, each having one flat outer end wall whose diameter substantially corresponds to the outside diameter of the cylindrical pipe section, and one concave interior end wall whose diameter is selected to be snugly received by the respective first or second open ends of the hollow cylinder, thereby defining an enclosed volume described by the inner dimensions of a central portion of the length of the hollow cylindrical pipe section and the concave interior walls of the first and second cylindrical blocks;
    (i) said firt cylindrical block having a centrally located threaded opening therethrough, to receive a line for the upwardly flowing entry of the liquid sample;
    (ii) said second cylindrical block having a centrally located threaded opening therethrough, to receive a line to accommodate the exit of the liquid sample; and
    (iii) said second cylindrical block additionally having a plurality of threaded openings extending therethrough and spaced about the centrally located opening, to receive at the flat outer wall of the second cylindrical block a plurality of selected analytical electrodes or sensors;
  (c) sealing means for effecting a liquid-tight seal between the open ends of the hollow cylindrical pipe section and the respective flat outer walls of the cylindrical blocks;
  (d) a plurality of interchangeable threaded electrodes or sensors, sealably fitted to the flat outer wall of the second cylindrical block and extending into a central portion of the enclosed volume; and
  (e) external meter means, attached to said electrodes or sensors for measurement of the characteristic parameters associated therewith.

15. The improved method of claim 14 wherein the concave interior end walls of the cylindrical blocks are concave conical interior end walls.

16. The improved method of claim 14 wherein the concave interior end walls of the cylindrical blocks are concave parabolic interior end walls.

17. The improved method of claim 14 wherein the hollow cylindrical pipe section is constructed of a transparent plastic material.

18. The improved method of claim 14 wherein the hollow cylindrical pipe section is constructed of polymethyl methacrylate pipe.

19. The improved method of claim 14 wherein the solid cylindrical blocks are constructed of a transparent plastic material.

20. The improved method of claim 14 wherein the solid cylindrical blocks are constructed of polymethyl methacrylate.

21. The improved method of claim 14 wherein the length of the hollow cylindrical pipe section is from about 1.5 to about 5 times the internal diameter of said pipe section.

22. The improved method of claim 14 wherein the overall length of the solid cylindrical blocks is from about 0.5 to about 1.0 times the internal diameter of said pipe section.

23. The improved method of claim 14 wherein the length of the pipe section is selected to provide inner dimensions of a central portion of said pipe length sufficient to avoid turbulent liquid flow in the central portion of the enclosed volume defined thereby.

24. The improved method of claim 14 wherein the ground water sample is analyzed for values of pH, oxidation-reduction potential, conductance, and temperature.

25. The improved method of claim 14 wherein the analytical cell is contained within a portable housing additionally fitted with a sampling line and a pump suited for field measurement of water streams or pools.

* * * * *